United States Patent [19]

Meyer

[11] Patent Number: 5,012,669

[45] Date of Patent: May 7, 1991

[54] OXYGEN SENSING METHOD AND APPARATUS

[75] Inventor: Emilio Meyer, Assago-Milano, Italy

[73] Assignee: Panametrics, Inc., Waltham, Mass.

[21] Appl. No.: 465,025

[22] Filed: Jan. 16, 1990

Related U.S. Application Data

[63] Continuation-in-part of Ser. No. 252,812, Oct. 3, 1988, Pat. No. 4,893,495.

[51] Int. Cl.⁵ .............................................. G01N 27/74
[52] U.S. Cl. .................................... 73/25.02; 324/204
[58] Field of Search ....................... 73/25.02; 324/204

[56] References Cited

U.S. PATENT DOCUMENTS

| | | | |
|---|---|---|---|
| 2,693,103 | 11/1954 | Krupp | 73/25.02 |
| 2,944,418 | 7/1960 | Engelhardt | 73/25.02 |
| 2,951,359 | 9/1960 | Krupp | 73/1 |
| 3,064,465 | 11/1962 | Richardson | 73/25.02 |
| 3,240,051 | 3/1966 | Lenfant | 73/25.02 |
| 3,276,244 | 10/1966 | Wilson et al. | 73/25.02 |
| 3,292,421 | 12/1966 | Meyer | 73/25.02 |
| 3,435,662 | 4/1969 | Meyer | 73/25.02 |
| 3,616,679 | 11/1971 | Meyer et al. | 73/25.02 |
| 3,646,803 | 3/1972 | Meyer | 73/25.02 |

FOREIGN PATENT DOCUMENTS

64957 6/1942 Denmark .

OTHER PUBLICATIONS

Paulding et al., 1946, "An Instrument for Determining the Partial Pressure of Oxygen in a Gas", Contribution from the Gates and Crellin Laboratories of Chemistry, California Institute of Technology, pp. 795-798.

Medlock, 1950, "Oxygen Analysis", pp. 1-8.

Ellis et al., 1968, "The Measurement of Gaseous Oxygen Tension Utilizing Paramagnetism: An Evaluation of the Servomex OA.150 Analyzer", Brit. J. Anaesth, vol. 40, pp. 569-578.

*Primary Examiner*—Hezron E. Williams
*Assistant Examiner*—Joseph W. Roskos
*Attorney, Agent, or Firm*—Lahive & Cockfield

[57] ABSTRACT

Apparatus for measuring concentration of a paramagnetic gas in a gas mixture includes first and second magnet pole pieces positioned adjacent each other with a selected gap therebetween, for generating an inhomogeneous magnetic field. The pole pieces have a sc⋯ ⋯d sectional shape, and a gap-facing surface with a s⋯ ⋯d configuration, that provide an elongated region o⋯ ⋯xi- mum magnetic field intensity in the gap. Electrically heated magnetic wind generating thermistors are positioned in the gap. Electrically heated magnetic wind sensing thermistors are positioned adjacent to the magnetic wind generating thermistors, proximate to the elongated region of maximum magnetic field intensity, such that a heated region associated with the wind generating and wind sensing thermistors is substantially encompassed by the elongated region of maximum magnetic field intensity. Consequently, only gas substantially within the region of maximum magnetic field intensity is subjected to heating and reduction of magnetic susceptibility, whereby gas outside the region of maximum magnetic field intensity is attracted with a selected maximum force.

6 Claims, 2 Drawing Sheets

W1, W2 = WIND GENERATING THERMISTORS
R1, R2 = WIND SENSING THERMISTORS (PRIOR ART) FIG. 3D

OXYGEN SENSING METHOD AND APPARATUS

REFERENCE TO RELATED APPLICATIONS

This application is a continuation-in-part of U.S. Pat. No. 4,893,495, issued Jan. 16, 1990, based on U.S. patent application Ser. No. 252,812, filed Oct. 3, 1988, for Oxygen Sensing Method and Apparatus.

The teachings of the above-cited parent application are incorporated herein by reference.

BACKGROUND OF THE INVENTION

This invention relates generally to oxygen sensing methods and apparatus, and, more particularly, relates to apparatus and methods for measuring oxygen concentration in gas mixtures by magnetic means.

Accurate measurement of oxygen concentration in a gas mixtures is critical to many industrial, clinical and laboratory processes, and a variety of devices have therefore been proposed or developed for measuring oxygen concentration. It has long been recognized that oxygen is paramagnetic, in that its molecules seek the strongest part of a magnetic field. Most other gases, in contrast, are diamagnetic, in that their molecules seek the weakest part of a magnetic field. The widely recognized paramagnetic properties of oxygen have stimulated a number of investigations into methods and apparatus for measuring oxygen concentration in gas mixture by magnetic sensing apparatus.

In particular, if a substance is placed in a magnetic field of strength H, the magnetic induction is given by B, where $$B = H + 4(\pi)(\zeta) \quad \text{Eq. (1)}$$

where the quantity (zeta) is the intensity of magnetization, and $$(\zeta)/H = k \quad \text{Eq. (2)}$$

is the magnetic susceptibility per unit volume.

Generally, the mass susceptibility of diamagnetic substances is independent of temperature and of field strength. The susceptibility of paramagnetic substances, however, is inversely proportional to the absolute temperature, and independent of field strength. Because the density is also inversely proportional to temperature, the susceptibility by volume is inversely proportional to the square of the temperature.

Any substance placed in a magnetic field develops an induced moment, analogous to the induced electric moment developed by a non-polar molecule in an electric field. A paramagnetic substance, however, has a permanent moment, similar to the permanent electric dipole moment of a polar molecule.

If a body is placed in a uniform magnetic field, it will experience an orienting effect, unless it is magnetically isotropic. The magnetic moment acquired by the body under these circumstances will be proportional to $kvH$, i.e., the product of volume, susceptibility per unit volume, and field intensity.

However, the body will experience no displacing force if the field is uniform. If the field is non-uniform, with a gradient $dH/dS$ in the direction S, the body will experience a linear displacing force in the direction S, and this linear displacing force F will be given by $$F = (kvh)(dH/dS) \quad \text{Eq. (3)}$$

that is, the force will be proportional to the product of the moment and the gradient.

If a sample of matter is placed between the poles of a magnet so that one part of the sample is in a region of large field strength and the other is in a region of negligible field, then the force acting on the sample is that described by Equation (3), integrated from the region of maximum field out to the region of negligible field. This integration gives a resultant force $$F = \tfrac{1}{2}(kH^2 A) \quad \text{Eq. (4)}$$

where A is the cross sectional area of the sample.

An early type of paramagnetic measuring cell, which relied upon the magnetic susceptibility of oxygen, is described in Pauling, et al, "An Instrument for Determining the Partial Pressure of Oxygen in a Gas", 68 *Journal of the American Chemical Society* 795, (1946). The Pauling et al measuring cell utilizes a sealed glass tube containing a weakly diamagnetic gas, such as nitrogen. The tube is suspended between the wedge-shaped pole pieces of a permanent magnet, which provide a non-uniform magnetic field, and the tube is free to rotate about a vertical axis. The entire structure is then placed within a chamber containing a selected gas.

When oxygen is introduced into the chamber surrounding the tube, the nitrogen in the tube is effectively diamagnetic relative to the surrounding paramagnetic oxygen gas, and the tube experiences a force tending to rotate it into the region where the magnetic field is weakest.

This rotation, or a force required to prevent this rotation, can be measured as an indication of the concentration of oxygen in the chamber. The Pauling cell, however, is fragile, and the rotational axis of the tube must be consistently oriented for each use, rendering it unsuitable for industrial oxygen measurement applications.

Another type of apparatus for measuring the concentration of oxygen relies upon the inverse relationship between temperature and the magnetic susceptibility of oxygen. To exploit this inverse relationship, a heating element can be used to heat a portion of an oxygen-containing mixture in a non-homogeneous magnetic field, thus creating a "magnetic wind" gas flow that can be measured by its thermal effect on adjacent thermistor elements.

In particular, the magnetic susceptibility of the sample gas is inversely proportional to the square of the temperature, and susceptibility can fall to negligible levels if the heating is sufficient. If the heating element provides incomplete or insufficient heating, however, the magnetic susceptibility of the sample remains significant. Under these circumstances, Equation (3) becomes $$F = \tfrac{1}{2}(k - k_o)(H^2 - H_o^2) A \quad \text{Eq. (5)}$$

where $k_o$ is the residual susceptibility and $H_o$ is the residual field intensity.

Various configurations of magnetic wind devices are discussed in Medlock, et al, "Oxygen Analysis", *Transactions of the Instruments and Methods Conference*, Stockholm, 1949, pp. 1–8; and Ellis, et al, "The Measurement of Gaseous Oxygen Tension Utilizing Paramagnetism", 40 *British Journal of Anaesthesia* 569 (1968).

Conventional magnetic wind oxygen measurement devices, unfortunately, are subject to relatively large errors due to the changes in the thermal properties of the surrounding, or "background" gases. In particular, the presence of different background gases causes conventional magnetic wind oxygen sensors to yield false readings of oxygen levels, due to the large differences in thermal characteristics of the background gases.

Prior magnetic wind oxygen sensing devices also suffer from position sensitivity and background gas dependency, especially in comparison with methods based on direct measurement of magnetic susceptibility.

Moreover, designers of paramagnetic gas sensors have heretofore assumed—based on the relationship between magnetic field gradient and the force experienced by a sample in a non-homogenous field—that in order to obtain a strong measurement signal, it is necessary to maintain a high magnetic field gradient and to locate the wind-generating resistance elements in the high gradient zone.

Proceeding on this assumption, certain prior art devices employ magnetic pole pieces shaped so as to generate a localized maximum magnetic field gradient, and utilize heating/sensing thermistors located in the high gradient zone. The heating effect of these thermistors, however, is not confined to the region of highest field intensity, but instead "leaks" into a second zone beyond the region of high field intensity. The elevated temperature reduces magnetic susceptibility in this second zone, and thus reduces the signal generated by the sensing thermistors. The configuration of certain conventional sensing devices, therefore, prevents the attainment of maximum measurement signal.

U.S. Pat. No. 3,064,465 of Richardson is an example of this configuration. The Richardson patent discloses a measurement device in which the magnetic pole pieces are shaped to provide a maximum magnetic gradient, and in which the heating effect of the heating thermistors extends beyond the point of highest field intensity, into the zone where should ideally have the lowest temperature to maximize the measurement signal. This reduction in measurement signal, caused by heating and susceptibility reduction outside of the zone of maximum field intensity, is a significant limitation of the prior art.

It is accordingly an object of the invention to provide oxygen sensing methods and apparatus which yield sensitive, accurate measurements of oxygen concentration, independent of background gas composition and thermal properties.

It is a further object of the invention to provide oxygen measurement apparatus which are rugged, reliable, and readily portable.

Other general and specific objects of the invention will in part be obvious and will in part appear hereinafter.

SUMMARY OF THE INVENTION

The foregoing objects are attained by the invention, which provides methods and apparatus for measuring the concentration of a paramagnetic gas in a gas mixture. One aspect of the invention includes magnetic field elements for generating an inhomogeneous magnetic field; wind generating and wind sensing thermistors for heating the gas to generate magnetic wind and sensing the magnetic wind in the presence of a paramagnetic gas; and signal generating elements, in electrical circuit with the thermistors, for measuring electrical resistance of the wind sensing thermistors and generating a measurement signal representative of the concentration of the paramagnetic gas and proportional to the magnitude of the magnetic wind.

The magnetic field elements include first and second pole pieces positioned adjacent each other, with a gap between the first and second pole pieces. The wind generating thermistors are positioned in the gap between the pole pieces on opposite sides of the gap, and the wind sensing thermistors are located adjacent the wind generating thermistors.

The pole pieces are shaped so as to produce an elongated region of high field intensity, and the thermistors are located in a selected position with respect to the pole pieces so that the region of high field intensity substantially encompasses the region heated by the wind generating thermistors—i.e., the heating effects of the wind generating thermistors are limited to a region of high magnetic field intensity. The heating effects of the wind sensing thermistors are limited to the zone of decreasing field intensity. The signal generating elements include a constant temperature electrical bridge, and a measurement electrical bridge in which the thermistors form the branches of a Wheatstone bridge. Current control elements, responsive to electrical imbalance between the constant temperature electrical bridge and the measurement bridge, control current to the Wheatstone bridge to maintain the thermistors at a substantially constant temperature.

The signal generating elements also include correction elements responsive to the electrical imbalance between the constant temperature electrical bridge and the measurement electrical bridge, for generating a correction signal, and combining elements for combining the correction signal and the measurement signal to correct the amplitude of the measurement signal responsive to changes in background gases in the gas mixture.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which:

FIGS. 3C and 3D are plots of magnetic field intensity versus position, and temperature versus position, for the conventional device illustrated in FIGS. 3A and 3B;

DESCRIPTION OF PREFERRED EMBODIMENTS

Figure 1:
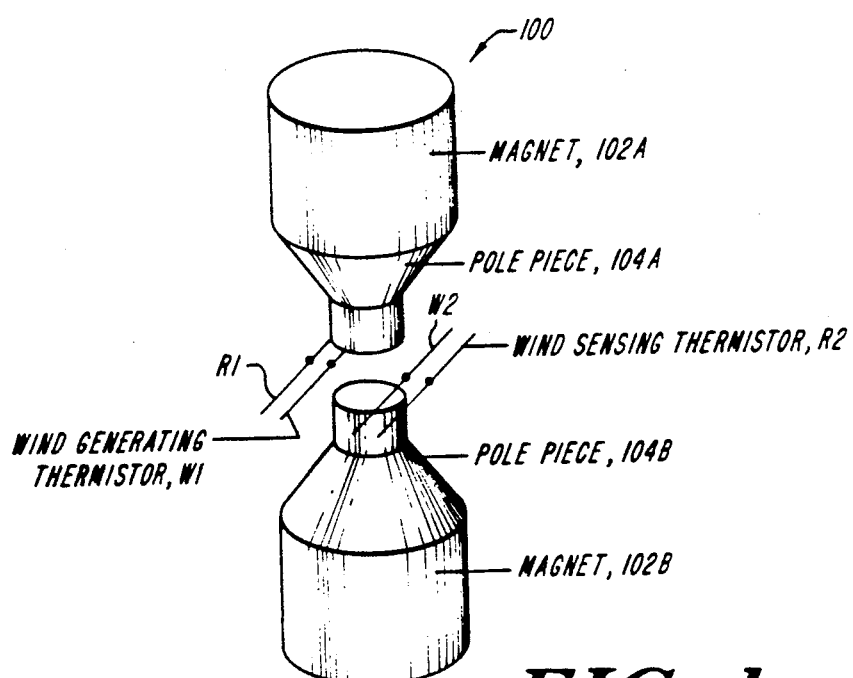
FIG. 1 is a schematic diagram depicting an oxygen sensing cell configured in accordance with the invention.

FIG. 1 is a schematic diagram depicting a configuration of an oxygen sensing cell in accordance with the invention. The oxygen sensor utilizes the "magnetic wind" phenomenon, and includes a sensor cell 100 having two pairs of electrically heated conventional thermistors R1, W1, and R2, W2.

One thermistor of each pair of electrically heated thermistors—i.e. thermistors W1 and W2—is located in a nonuniform magnetic field of high intensity. The second thermistor of each pair of electrically heated thermistors—i.e. thermistors R1 and R2—is located adjacent to W1 and W2, respectively, but selectively offset from the region of highest magnetic field intensity. The sectional shape of the pole pieces and the offset of the outside thermistors from the region of highest magnetic field intensity is discussed in greater detail hereinafter in connection with FIGS. 4A–4D.

When oxygen is present in the oxygen sensing cell 100, and thermistors W1 and W2 are electrically heated, thermistors W1 and W2 generate a gas flow in the direction of the adjacent thermistors of each pair offset from the maximum magnetic field—i.e. thermistors R1 and R2. The thermistors W1 and W2 thus lose heat to the adjacent thermistors R1 and R2 of each pair. Accordingly, the presence of oxygen in the oxygen sensing cell 100 tends to proportionally reduce the temperature of the thermistors W1 and W2, and tends to increase the temperature of the adjacent thermistors R1 and R2.

The illustrated arrangement of sensor cell 100 minimizes the background gas dependency which would otherwise result from variations in thermal conductivity, heat capacity and viscosity. Moreover, the thermistor pairs can be precisely located to maximize signal output, as described in greater detail below in connection with FIGS. 4A–4D.

Figure 2:
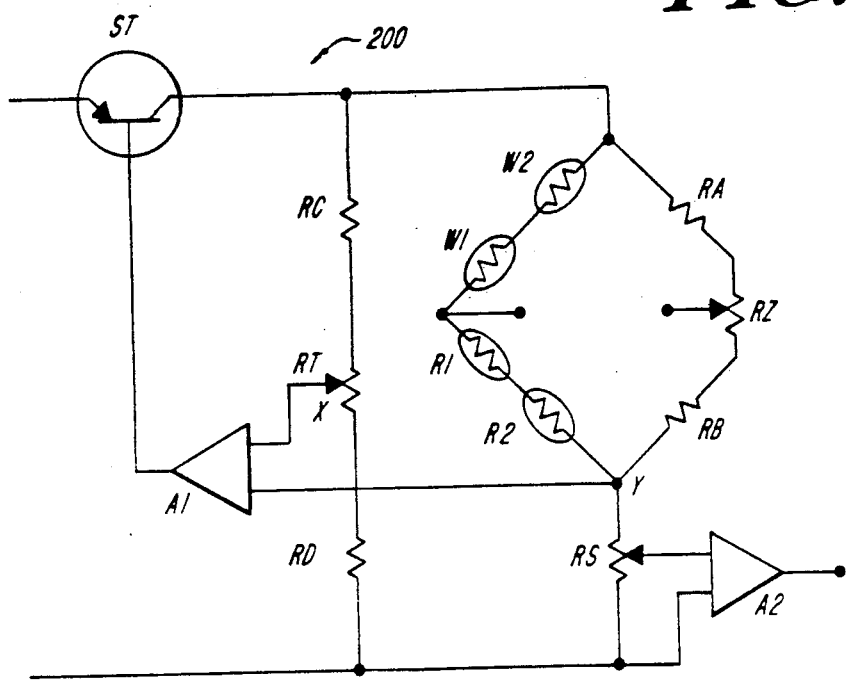
FIG. 2 is a schematic diagram depicting an oxygen sensing circuit in accordance with the invention.

In a preferred embodiment of the invention, the thermistor pairs R1, W1 and R2, W2 are additively connected in a measuring bridge circuit illustrated in FIG. 2. The measuring bridge circuit 200 is unbalanced, due to the resistance change resulting from the thermistor temperature unbalance. This thermistor temperature unbalance, in turn, is proportional to oxygen concentration.

In accordance with the invention, the circuit illustrated in FIG. 2 eliminates the undesirable effects of ambient temperature variations by controlling the temperature of the oxygen sensing elements. The temperature of the oxygen sensing elements is maintained at a substantially constant level by a high precision temperature control loop that includes the illustrated series transistor ST and bridge temperature adjusting element RT. In particular, the illustrated circuit 200 includes a constant temperature bridge, formed by resistors RC, RD, RS, and the oxygen measuring bridge consisting of thermistors W1, W2, R1, R2, RA, and resistances RB and RZ.

Resistors RC, RD, RS, and the oxygen measuring bridge consisting of thermistors W1, W2, R1, R2, RA, and resistances RB and RZ, form the four arms of a Wheatstone bridge. Variable resistor RT is utilized as a bridge temperature adjustment element. Amplifier A1, which can be of conventional design and construction, detects any electrical unbalance between nodes "X" and "Y" and drives the series transistor ST to change the bridge current so as to restore the bridge balance.

This detection and control loop maintains the elements of the oxygen measuring bridge at constant temperature, regardless of any variation in background gas composition that would otherwise affect, through changes in thermal conductivity, the thermistor heat dissipation and temperature. The optimum temperature of the thermistors, in the absence of oxygen, has been found to be approximately 200 C.

An important advantage of the circuit illustrated in FIG. 2 is that the thermistors are maintained at constant temperature. This constant temperature maintains a constant thermal relationship between the thermistor pairs R1, W1, and R2, W2 of the sensing cell 100 illustrated in FIG. 1, thereby minimizing errors in oxygen readings caused by variations in the thermal properties of background gases.

A further advantage of the illustrated configuration is the ability to obtain a signal, at the output of amplifier A2, which can be used as a correction signal, or multiplier, for accurately correcting errors in the oxygen reading obtained from the measuring bridge due to variations of thermal properties of the sample. This signal is obtained by sensing through RS the current change necessary to restore the bridge balance. These advantages are best illustrated by way of an example of oxygen measurement utilizing a conventional magnetic wind oxygen sensor. Assume, for example, that a measurement of oxygen is required over a 0% to 5% range, in a gas stream consisting of oxygen, nitrogen, carbon dioxide and hydrogen. In a conventional magnetic wind oxygen analyzer, the measuring bridge is adjusted to yield a zero oxygen reading in 100% nitrogen, and for full scale oxygen reading with 5% oxygen and 95% nitrogen. The conventional magnetic wind oxygen sensor will then provide correct oxygen measurements, within the limits of overall analyzer accuracy, of any oxygen concentration within the measuring range of 0–5% oxygen. The conventional oxygen analyzer, however, will yield a lower-than-true value when the nitrogen background gas is replaced by hydrogen. In particular, a conventional oxygen sensor may yield a reading as low as 20% of the correct value. The converse problem results when the nitrogen background gas is replaced by carbon dioxide. In this case, a conventional magnetic wind oxygen sensor will yield an oxygen reading as high as twice the correct value. The above errors, which are typical of prior art magnetic wind oxygen sensors, are due to the large differences in the thermal properties of hydrogen and carbon dioxide in comparison to nitrogen. These differences in thermal properties greatly affect the heat transfer from the wind generating thermistors to the adjacent wind sensing thermistors.

In accordance with the invention, however, the change in the bridge current necessary to compensate for the above variations and to restore the balance between "X" and "Y" is sensed through RS and amplified and scaled by A2, which supplies a correction signal that can be used as a multiplier for the signal supplied by the oxygen measuring bridge. This correction signal is utilized to correct the oxygen measuring bridge signal in units of percent oxygen, regardless of changes in the background gas composition.

By adjusting the gain and the bias of amplifier A2, the output of A2 can be made either proportional to, or inversely proportional to the thermal effects. The circuitry used to combine the correction signal and the measurement signal to correct for changes in thermal properties of the background gases can thus be either a multiplier or a divider circuit.

The structure and operation of the oxygen sensor of FIGS. 1 and 2 is further described in commonly-owned U.S. Pat. No. 4,893,495, issued Jan. 16, 1990, based on U.S. patent application Ser. No. 252,812 (Attorney Docket PMH-126), filed Oct. 3, 1988, for Oxygen Sensing Method and Apparatus, incorporated herein by reference.

As discussed above in connection with FIG. 1, the thermistor pairs can be located in selected positions to maximize measurement signal output. The sectional shape of the pole pieces and the configuration of pole piece gap can also be selected to enhance signal output. The effect of pole piece and thermistor configuration—and, more particular, the signal-generating advantage of the invention over the prior art—are best illustrated by comparison of the invention with the prior art, with reference to FIGS. 3A-3D and FIGS. 4A-4D.

Figure 3A:
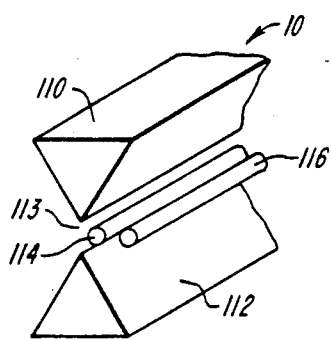
FIGS. 3A and 3B are simplified schematic diagrams depicting a conventional paramagnetic gas sensing device having a pole piece and thermistor configuration typical of the prior art.
Figure 3B:
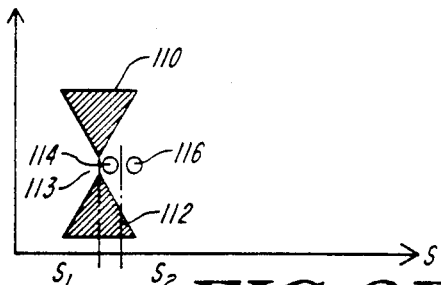

FIGS. 3A and 3B are simplified schematic diagrams depicting a conventional paramagnetic gas sensing device 10 having a configuration of pole pieces 110, 112 and thermistors 114, 116 typical of the prior art. For simplicity, only one pair of thermistors 110, 112 is illustrated. Those skilled in the art will appreciate that a second pair of thermistors can be symmetrically situated on the opposite side of the pole piece gap 113.

Figure 3C:
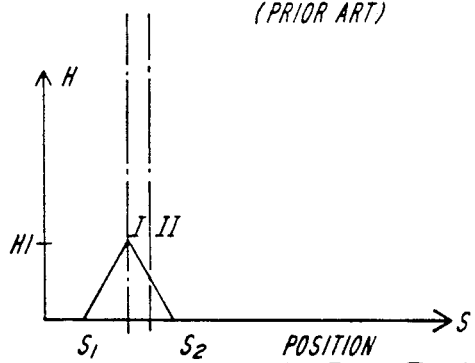

FIGS. 3C and 3D, respectively, show a graph of typical magnetic field intensity values H versus position S, and a graph of typical temperature values T versus position S, for the conventional configuration depicted in FIGS. 3A and 3B. FIGS. 3C and 3D are aligned with FIG. 3B so that S-axis values S1 and S2, respectively, are the same for each drawing figure.

Figure 4A:
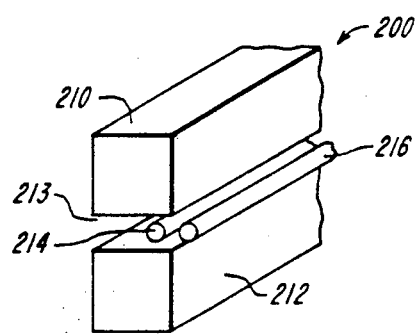
FIGS. 4A and 4B are simplified schematic diagrams depicting pole piece and thermistor configuration for a paramagnetic gas sensing device according to the invention.
Figure 4B:
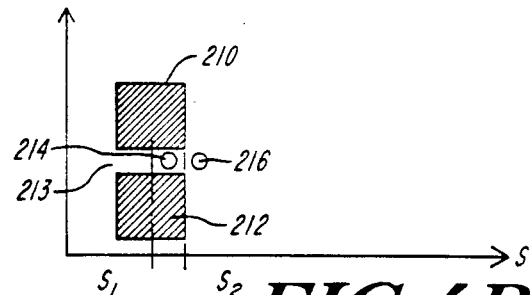
Figure 4C:
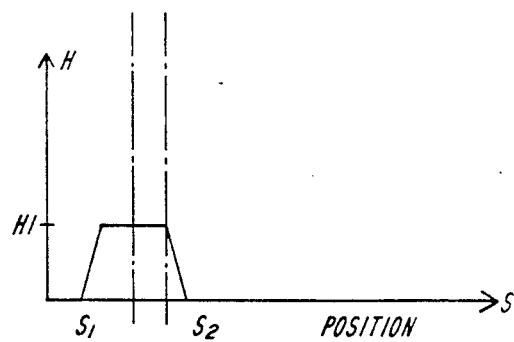
FIGS. 4C and 4D depict magnetic field intensity versus position and temperature versus position for the embodiment of FIGS. 4A and 4B.
Figure 4D:
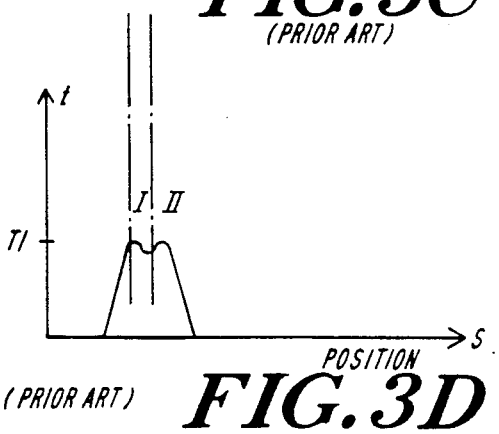
Figure 4D:
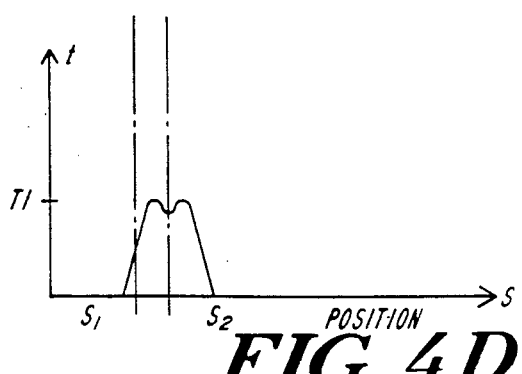

FIGS. 4A and 4B, in turn, are simplified schematic diagrams depicting a configuration of pole pieces 210, 212 and thermistors 214, 216 for a paramagnetic gas sensing device 200 according to the invention. Again, while only one pair of thermistors 210, 212 is illustrated, a second pair can be symmetrically situated on the opposite side of the pole piece gap 213. FIGS. 4C and 4D, respectively, depict typical magnetic field intensity values H versus position S, and typical temperature values T versus position S for the embodiment of FIGS. 4A and 4B.

As FIGS. 3A-3C indicate, the pole pieces used in prior art devices are shaped so as to produce a maximum magnetic field gradient. In particular, the pole pieces 110 and 112 are substantially triangular in section at the region proximate the pole piece gap 113. Magnetic field intensity H increases rapidly with S-axis position, to a maximum of H1 corresponding to S-axis position S1. This S-axis position, in turn, corresponds to point at which the vertices of the triangular sections of pole pieces 110, 112 are closest. The magnetic field intensity H then falls off rapidly with S-axis positions greater than S1.

Moreover, as FIG. 3A shows, the heating effect of the thermistors 114, 116—as indicated in the temperature/position graph of FIG. 3D—"leaks" past the region of highest field intensity around S1 (indicated as region I in FIGS. 3C and 3D). The elevated temperature reduces the magnetic susceptibility of the sample gas in the outlying region (i.e., region II of FIGS. 3C and 3D) and therefore reduces the amplitude of the measurement signal generated by the sensing thermistors. More particularly, the otherwise "cold" gas in region II (FIG. 3D), which should be at relatively low temperature to maximize signal, is undesirably heated by the operation of the conventional arrangement.

The invention, as depicted in FIGS. 4A-4D, avoids this problem by utilizing pole piece sectional shapes and a pole piece gap form that provide an elongated region of maximum magnetic field intensity, and thermistors that are positioned, with respect to the magnetic field, such that the heating effect of the thermistors is substantially limited to the region of highest field intensity.

FIG. 4A depicts an oxygen sensing device according to the invention, having pole pieces 210, 212 and thermistors 214, 216. Unlike the pole pieces 110, 112 illustrated in FIGS. 3A and 3B, the pole pieces 210, 212 depicted in FIGS. 4A and 4B are substantially rectangular in section at the region nearest pole piece gap 213, and each pole piece has a substantially planar surface proximate gap 213. Those skilled in the art will appreciate that other pole piece sectional shapes and gap forms can be utilized in accordance with the invention, to provide an elongated region of high magnetic field intensity.

In operation, during the flow of gas associated with the magnetic wind, upstream thermistor 214 is cooled by the gas flow, and downstream thermistor 216 is heated by the flow. Both thermistors 214, 216 heat the sample gas and thus reduce its magnetic susceptibility.

In the device illustrated in FIG. 4A and 4B, the heating/sensing thermistors 214, 216 are located partially within the magnetic field. Unlike the configuration depicted in FIGS. 3A-3D, the magnetic field intensity H produced by pole pieces 210, 212 does not fall off rapidly past position S1. Instead, the field intensity remains constant, at its maximum value H1, between positions S1 and S2. Thus, because of the substantially planar shape of the proximal surfaces of pole pieces 214, 216—i.e., the constant gap width provided by the surfaces facing gap 213—the zone of high magnetic field strength is elongated or expanded, as compared with the magnetic field produced by conventional pole pieces 110, 112 (FIGS. 3A-3C).

Accordingly, as FIGS. 4C and 4D indicate, the heating zone of the thermistors 214, 216 is substantially encompassed by the expanded region of high magnetic field strength generated by pole pieces 210, 212. In effect, the heating caused by the thermistors is substantially precluded from affecting the zone of opposite magnetic gradient where cold sample gas is entering the magnetic field.

Moreover, although Equation 3 above suggests that a lower gradient around S1 would result in a reduction of observed magnetic force, such a reduction does not occur. This is because the magnetic force is described by integration over all layers from high field to negligible field (Equation 4 above), and in accordance with the invention, this integration occurs over an elongated path.

It will thus be seen that the invention efficiently attains the objects set forth above. In particular, the invention provides accurate measurement of oxygen concentration, independent of changes in background gas composition. The invention also provides extremely good zero and span stability with low drift, and allows for a compact sensor which can be removed for calibration checks in the laboratory, without breaking electrical or pneumatic connections.

It will be understood that changes may be made in the above construction and in the foregoing sequences of operation without departing from the scope of the invention. Other pole piece sectional configurations, for example, may be employed to provide a substantially constant pole piece gap and an expanded region of maximum magnetic field intensity. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

What is claimed is:

1. In apparatus for measuring the concentration of a paramagnetic gas in a gas mixture, the improvement comprising magnetic field means for generating an inhomogeneous magnetic field, said magnetic field means including first and second magnet pole pieces, said first and second magnet pole pieces having a selected sectional shape, said first and second magnet pole pieces being positioned adjacent each other with a selected gap between said first and second magnet pole pieces, said first and second magnet pole pieces each having a gap-facing surface having a selected configuration, said selected sectional shape of said first and second magnet pole pieces, and said selected configuration of said gap-facing surfaces, providing an elongate region of maximum magnetic field intensity in said gap, magnetic wind generating thermistor means, including at least one electrically heated magnetic wind generating thermistor, for generating a magnetic wind in the presence of a paramagnetic gas, the magnetic wind having a magnitude proportional to concentration of the paramagnetic gas in the gas mixture, said at least one wind generating thermistor having an electrical parameter proportional to temperature, said at least one wind generating thermistor being positioned within said gap and inside said inhomogeneous magnetic field, magnetic wind sensing thermistor means, including at least one electrically heated magnetic wind sensing thermistor, said at least one magnetic wind sensing thermistor having an electrical parameter proportional to temperature, for sensing the magnetic wind generated by said at least one magnetic wind generating thermistor in the presence of a paramagnetic gas, said at least one magnetic wind sensing thermistor being positioned adjacent to said at least one magnetic wind generating thermistor, proximate to said elongate region of maximum magnetic field intensity, such that a heated region associated with said at least one magnetic wind generating thermistor and said at least one magnetic wind sensing thermistor is substantially encompassed by said elongate region of maximum magnetic field intensity, so that only gas substantially within the elongate region of maximum magnetic field intensity is subjected to heating and reduction of magnetic susceptibility, whereby gas outside the elongate region of maximum magnetic field intensity is attracted with a selected maximum force.

2. In apparatus according to claim 1, the further improvement wherein at least a portion of each of said first and second magnet pole pieces proximate said gap is substantially rectangular in section.

3. In apparatus according to claim 1, the further improvement wherein at least a portion of each said gap-facing surface is substantially planar.

4. In apparatus according to claim 1, the further improvement wherein at least a portion of said gap between said first and second magnet pole pieces has a dimension, in a direction normal to one gap-facing surface, substantially constant along said one gap-facing surface.

5. In apparatus according to claim 1, the further improvement comprising temperature control means for automatically maintaining said at least one magnetic wind generating thermistor and said at least one magnetic wind sensing thermistor at a substantially constant temperature.

6. In apparatus according to claim 5, the further improvement comprising signal generating means, in electrical circuit with said magnetic wind generating thermistor means and said magnetic wind sensing thermistor means, for measuring said electrical parameter of said at least one magnetic wind sensing thermistor and generating a measurement signal having an amplitude representative of the concentration of the paramagnetic gas in the gas mixture and proportional to the magnitude of the magnetic wind in the presence of the paramagnetic gas, said signal generating means including a constant temperature electrical bridge and a measurement electrical bridge, said measurement bridge including a Wheatstone bridge having branches including said at least one magnetic wind generating thermistor and said at least one magnetic wind sensing thermistor, correction means responsive to electrical imbalance between said constant temperature electrical bridge and said measurement electrical bridge, for generating a correction signal, and combining means for combining said correction signal and said measurement signal to correct said amplitude of said measurement signal responsive to changes in background gases in the gas mixture.

* * * * *